(12) United States Patent  
Moder et al.

(10) Patent No.: US 6,380,455 B1
(45) Date of Patent: Apr. 30, 2002

(54) FEMININE SANITARY PROTECTION PACKAGE AND METHOD

(75) Inventors: Susan Jean Moder; Richard William Kubalek, both of Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/473,836

(22) Filed: Dec. 28, 1999

(51) Int. Cl.[7] .......................... A61F 13/15; A61B 17/06
(52) U.S. Cl. .................... 604/358; 604/904; 206/440
(58) Field of Search ................. 604/385.01, 385.03, 604/385.04, 358, 904, 385.05, 385.06, 385.18; 206/225, 226, 438, 440, 570, 574, 581

(56) References Cited

U.S. PATENT DOCUMENTS

| | | |
|---|---|---|
| 2,092,346 A | 9/1937 | Arone |
| 3,062,371 A | 11/1962 | Patience |
| 3,698,549 A | 10/1972 | Glassman |
| 3,881,490 A | 5/1975 | Whitehead et al. |
| 3,963,029 A | 6/1976 | Brooks |
| 4,372,312 A | 2/1983 | Fendler et al. |
| 4,425,130 A | 1/1984 | DesMarais |
| 4,579,556 A | 4/1986 | McFarland |
| 4,648,513 A | 3/1987 | Newman |
| 4,781,712 A | 11/1988 | Barabino et al. |
| 4,834,737 A | 5/1989 | Khan |
| 4,848,572 A | 7/1989 | Herrera |
| 5,046,620 A | 9/1991 | Barabino |
| 5,048,589 A | 9/1991 | Cook et al. |
| 5,117,981 A | 6/1992 | Crawford et al. |
| 5,133,457 A | 7/1992 | Kadel |
| 5,180,059 A | 1/1993 | Shimatani et al. |
| 5,248,309 A | 9/1993 | Serbiak et al. |
| 5,350,067 A | 9/1994 | Beltran |
| 5,383,868 A | 1/1995 | Hyun |
| 5,399,412 A | 3/1995 | Sudall et al. |
| H1454 H | 6/1995 | Cucuzza et al. |
| 5,429,627 A | 7/1995 | Johnson et al. |
| 5,569,228 A | 10/1996 | Byrd et al. |
| 5,579,916 A | 12/1996 | Manko |
| 5,609,588 A | 3/1997 | DiPalma et al. |
| 5,618,282 A | 4/1997 | Schlangen |
| 5,649,916 A | 7/1997 | DiPalma et al. |
| 5,807,372 A | 9/1998 | Balzar |
| 5,827,251 A | 10/1998 | Moder et al. |
| 5,891,127 A | 4/1999 | Moder et al. |
| 5,954,201 A | 9/1999 | Finch et al. |
| 5,964,741 A | * 10/1999 | Moder et al. ............... 604/358 |
| 5,986,165 A | * 11/1999 | Moder et al. ............... 604/358 |
| 5,993,430 A | 11/1999 | Gossens et al. |

FOREIGN PATENT DOCUMENTS

| | | |
|---|---|---|
| DE | 3923289 A1 | 10/1990 |
| EP | 0 699 427 B1 | 6/1999 |
| WO | WO 88/10219 A1 | 12/1988 |
| WO | WO 99/30659 A1 | 6/1999 |
| WO | WO 99/52485 A1 | 10/1999 |

* cited by examiner

Primary Examiner—Dennis Ruhl
(74) Attorney, Agent, or Firm—Douglas L. Miller; Karl V. Sidor

(57) ABSTRACT

The feminine sanitary protection package and method provide a vaginal insertion device and a panty shield configured to fit the pudendal region of a woman. The panty shield is tri-folded over the vaginal insertion device. A pouch contains the combination including the panty shield and the vaginal insertion device. The pouch provides for transporting and disposing of the panty shield and vaginal insertion device.

18 Claims, 6 Drawing Sheets

FEMININE SANITARY PROTECTION PACKAGE AND METHOD

BACKGROUND OF THE INVENTION

The present invention relates to a feminine sanitary protection package and method for protecting a user by absorbing and containing menstrual fluids and other body exudes. More specifically, this invention relates to a novel feminine sanitary protection package which provides substantially full and complete sanitary protection, ease in handling, and discretion in packaging appearance.

Absorbent articles are designed to absorb body fluids, including menses, and may come in different functional designs. In one design category, sanitary napkins are externally worn about the pudendal area and are designed primarily for heavy flow. In another category, panty liners or panty shields are thin products externally worn about the pudendal area and are designed for light flow. In yet another category, tampons are designed to be positioned internally within the vagina.

Sanitary napkins can have high absorptive capacity with either a thin or thick absorptive element. However, compressive forces of the wearer's thighs and pudendal region during any physical movement, such as walking, can cause the sanitary napkin to shift from an original position protecting the vulva area. After a relatively short period of time, the sanitary napkin may move away from the vaginal orifice. The wearer's movement, particularly vigorous movement such as rapid walking or running, also can cause discomfort such as by rubbing or chafing in the sensitive vulva area.

In addition to concerns of sanitary napkin movement and discomfort, a concern of high degree of wearing awareness is present. Some thick sanitary napkins have a high profile appearance when viewed through a wearer's outer garments. The sanitary napkins can be very apparent when worn with tight fitting clothing including slacks, body suits, swimming suits, or similarly thin or close fitting outer garments.

Panty liners or panty shields have been developed for light or low menstrual flows. Some panty liners or panty shields have the same concerns associated with sanitary napkins, although their thin profile makes them more flexible, less noticeable in appearance, and generally more comfortable than the bulky sanitary napkins. However, the thin-profile panty liners or panty shields can have a drawback in the performance area of absorptive capacity.

Tampons, are worn internally within the vaginal canal to intercept body fluid. Sometimes tampons may not function completely to prevent leakage because radial expansion of the tampon within the vaginal canal does not form a perfect seal. Yet without such radial expansion and swelling of the tampon within the vaginal canal, the tampon does not serve as a completely reliable sanitary protection device.

In an attempt to address the above stated problems, a sanitary napkin or a panty liner is rolled about a tampon or similar device, and then inserted into a pouch. Thus, the user would have available a tampon or other similar device and either a sanitary napkin or a panty liner for use.

However, additional problems arise associated with a napkin or panty liner rolled about a tampon or other similar device. One of these problems is that the napkin or panty liner can tend to curl after removal from the pouch, thereby making it more difficult to adhere the curled napkin or panty liner onto an undergarment.

Another problem associated with a rolled napkin or panty liner is the possible loss of comfort and absorbency due to the undesired shape of a curled or partially curled napkin or panty liner.

Still another problem associated with a rolled napkin or panty liner is the potential loss of the embossing pattern on the cover, or the loss of some other cover characteristic.

SUMMARY OF THE INVENTION

In response to the discussed difficulties and problems encountered in the prior art, a feminine sanitary protection package and method have been discovered.

In one form of the present invention there is provided a feminine sanitary protection package comprising a vaginal insertion device, a panty shield tri-folded over the vaginal insertion device to form a combination including the panty shield and the vaginal insertion device. A pouch is provided for containing the combination, and further provides a feature for transporting and disposing of the combination.

In another form of the present invention there is provided a feminine sanitary protection package comprising a vaginal insertion device, a panty shield folded over the vaginal insertion device to form a combination including the panty shield and the vaginal insertion device. A release strip is provided on the panty shield for attaching it to a garment. A pouch contains the combination, and provides a feature for transporting and disposing of the combination.

In still another form of the present invention there is provided a method for providing a feminine care sanitary protection package comprising the steps of (a) providing a vaginal insertion device, (b) providing a panty shield, (c) tri-folding the panty shield over the vaginal insertion device to form a combination including the panty shield and the vaginal insertion device, and (d) providing a pouch for the combination for transporting and disposing of the combination:

BRIEF DESCRIPTION OF THE DRAWINGS

The above-mentioned and other features of the present invention and the manner of attaining them will become more apparent, and the invention itself will be better understood by reference to the following description of the invention, taken in conjunction with the accompanying drawings wherein.

DETAILED DESCRIPTION

Figure 2:
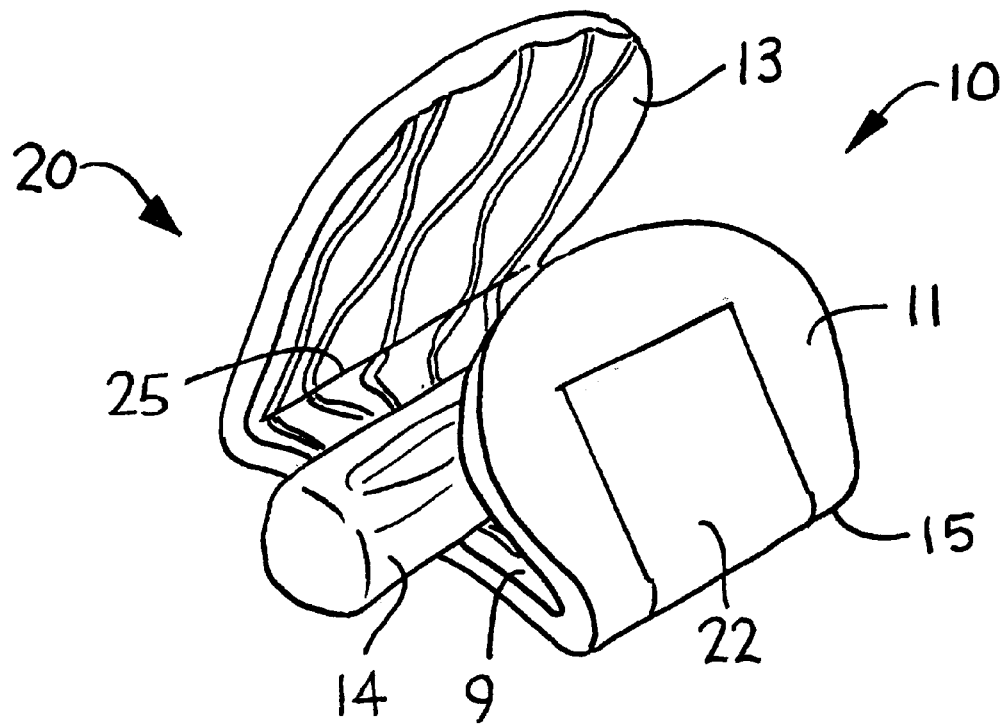
FIG. 2 illustrates a perspective view of the combination of FIG. 1 in a partially tri-folded form.

The feminine sanitary protection package and method of the present invention provide a panty liner or panty shield folded over one or more vaginal insertion devices containing absorbents or medical devices for easy handling, use, and proper disposal. The term "folded" refers, by way of example only, to a C-fold or to a tri-fold as illustrated in FIG. 2. The term "folded over" or variations thereof means the liner or shield has, for example the tampon positioned within the folds. The term "vaginal insertion device" refers to a vaginal insert or vaginal insert applicator. By "vaginal insert", it is meant, by way of example only, a tampon or vaginal medicinal insert such as a vaginal suppository. By "vaginal insert applicator", it is meant, by way of example only, a tampon applicator or a vaginal medicinal insert applicator such as a vaginal suppository applicator.

The present invention fills a woman's need to have a panty shield or liner readily accessible when using absorbent devices, such as tampons, or vaginal suppositories for yeast or other infections.

In one aspect, the present invention includes a pouch and a combination of, for example, a panty liner or panty shield folded over one or more devices containing absorbents, or medical devices. This combination provides a more discreet, convenient, and portable option than carrying the devices separately. The pouch, made with biodegradable and/or non-biodegradable materials, serves to protect the adhesive element prior to wear, and acts as a packaging agent for both devices. The present invention further provides efficiencies in material and manufacturing costs, and ease in consumer handling.

One advantage of the present invention is that it conveniently contains the devices or products a woman needs to feel fresh and completely protected from stains on her undergarments or adjacent clothing. The present invention also provides a woman with an almost zero chance of experiencing staining on her undergarments when using these products or devices together.

Another advantage of the present invention is that it is more discreet and convenient than carrying two or more separate devices. Thus, a woman does not need to go out and buy two or more separate devices, thereby saving money and time. Nor does she need to carry them around separately, and make sure when it comes time to use them that all of the separate devices or products still are available. The pouch keeps them fresh and protected from contamination.

The pouch of the present invention can be a separate pouch for transporting the combination of the panty liner or panty shield and device. The pouch keeps the combination clean, e.g., when the combination is kept and carried in a woman's purse, a brief case, backpack, or the like.

The pouch also provides a means for properly disposing of the combination of the panty liner or panty shield and device. The pouch can be composed of a plastic material, such as polyethylene or polypropylene, but may be composed of other materials, e.g., such as polyethylene oxide (PEO), polyvinyl alcohol (PVOH), polycaporolactone (PCL), paper, or a nonwoven material, e.g., such as spunbond/meltblown.

Referring now to the drawings, common elements in all of the drawings are referenced using the same identifying numerals.

Figure 1:
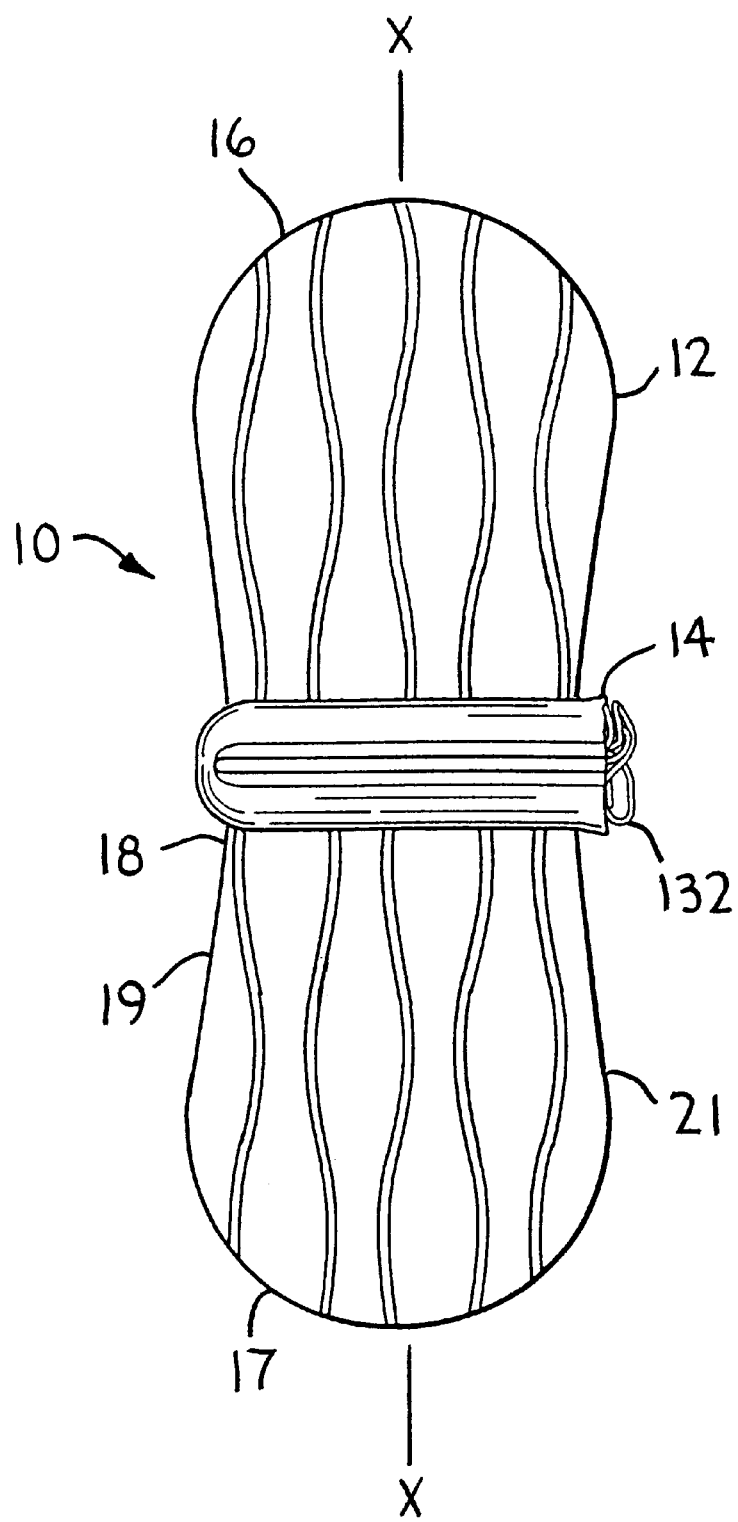
FIG. 1 illustrates an elevational view of a combination of a panty shield and a tampon.
Figure 3:
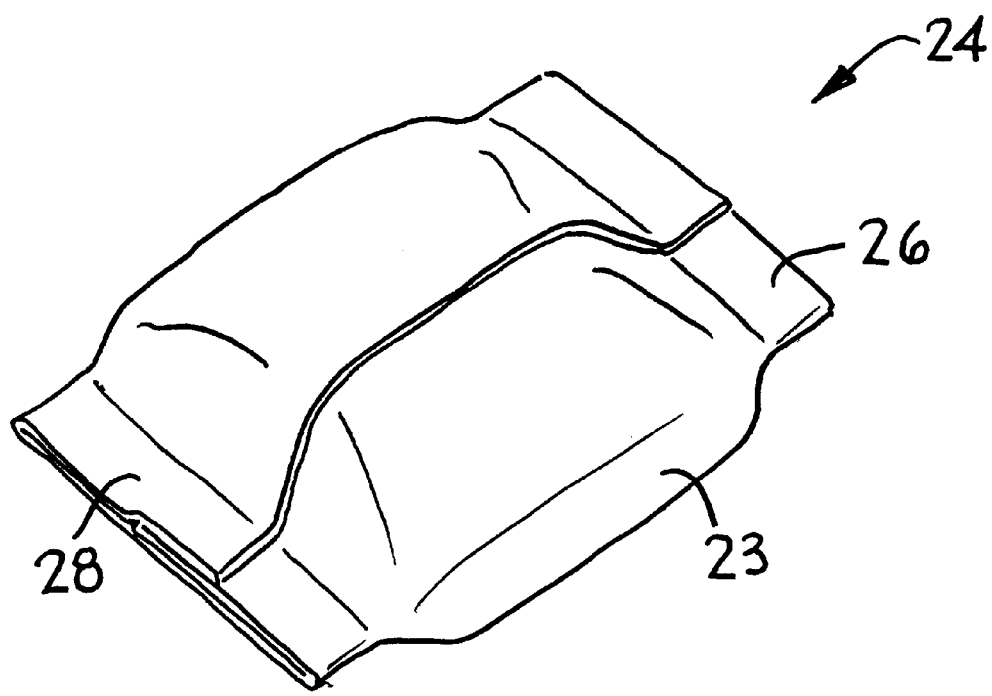
FIG. 3 illustrates a perspective view of a pouch containing the fully tri-folded combination of FIG. 2.

Referring to FIGS. 1–3, a sanitary protection device 10 includes a panty shield, liner, or the like 12 (hereafter, and for ease of reference in describing the invention, "liner, or the like" will not be referred to with numeral 12, but it is understood that numeral 12 includes a "liner, or the like") and a vaginal insertion device, such as a tampon 14. The panty shield 12 has an hourglass shape, but can have an oval, straight, racetrack shape, or other shape, having a first end 16, a second end 17, a first side 19, a second side 21 and a middle section 18. The panty shield 12 has a central longitudinal axis X—X. The tampon 14 is shown placed in a position near the middle section 18 and is positioned generally transverse to the length of the device 10 and to the longitudinal axis X—X of panty shield 12. The panty shield 12 is tri-folded over the tampon 14, for example by folding at fold lines 15, 25 (FIG. 2) to form generally planar fold panels 11, 13. Once folded, the fold panels 11, 13 and a base panel 9 are generally parallel to each other, thereby forming a generally hexahedral shape. The shield 12 and tampon 14 are folded in such a manner that a conventional release strip 22 of the panty shield 12 is showing, i.e., facing outwardly toward the user, on the exterior of the folded shield 12, as illustrated in FIG. 2. The folded combination 20 including the shield 12 and the vaginal insertion device, such as tampon 14, is placed in a separate pouch 23 having closed or sealed ends 26, 28, thereby forming a feminine sanitary protection package 24. The package 24 can be closed at both ends 26 and 28 by ultrasonic sealing, heat sealing, adhesive sealing, embossing, or any other means well known in the art.

Due to the tri-folded shape of panty shield 12 over tampon 14, several advantages are created. One of these is the elimination of the curling tendency associated with those prior art napkins or panty shields that are rolled about a tampon or other similar device. Upon removing tri-folded panty shield 12, it can be easily smoothed-out along fold lines 15, 25, thereby reassuming its desired shape or form, and allowing the panty shield to be easily adhered onto an undergarment.

Another advantage with the present invention is that the tri-folded panty shield 12 does not diminish the comfort or absorbency in the Z-direction, which is associated with those earlier attempts with a rolled napkin or panty liner.

Still another advantage with the present invention is that the tri-folded panty shield 12 will not loose Its embossing or other surface characteristic, which can exist with those earlier attempts utilizing a rolled napkin or panty liner.

Figure 4:
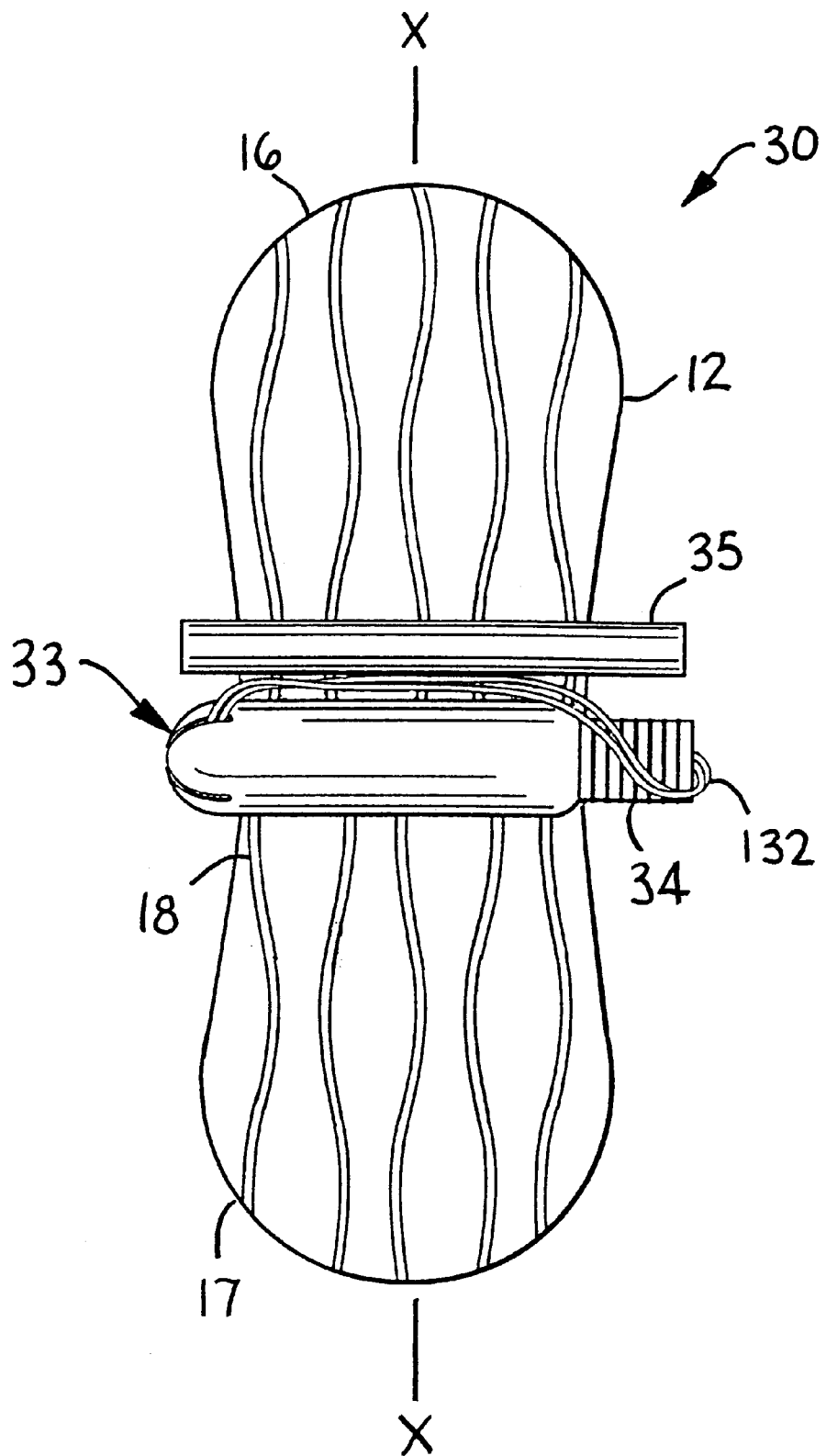
FIG. 4 illustrates an elevational view of a combination of a panty shield and a tampon applicator.

Referring now to FIG. 4, a sanitary protection device 30 includes a panty shield 12 and a different vaginal insertion device, such as a tampon applicator outer tube 34 and a plunger 35. A tampon having withdrawal string 132 is positioned in the outer tube 34, and the plunger 35 is designed to be inserted into the outer tube 34. The tampon applicator 33, having an outside tube 34 and a plunger 35, is shown placed in a position near middle section 18. Both the outside tube 34 and the plunger 35 are positioned generally transverse to the length of the device 30 and to the longitudinal axis X—X of the panty shield 12. The panty shield 12 is tri-folded over the tampon applicator 34 and plunger 35 in a manner similar to that with reference to shield 12 and tampon 14 in FIGS. 1–3, and can be packaged in a pouch 23, similar to that in FIG. 3.

Figure 5:
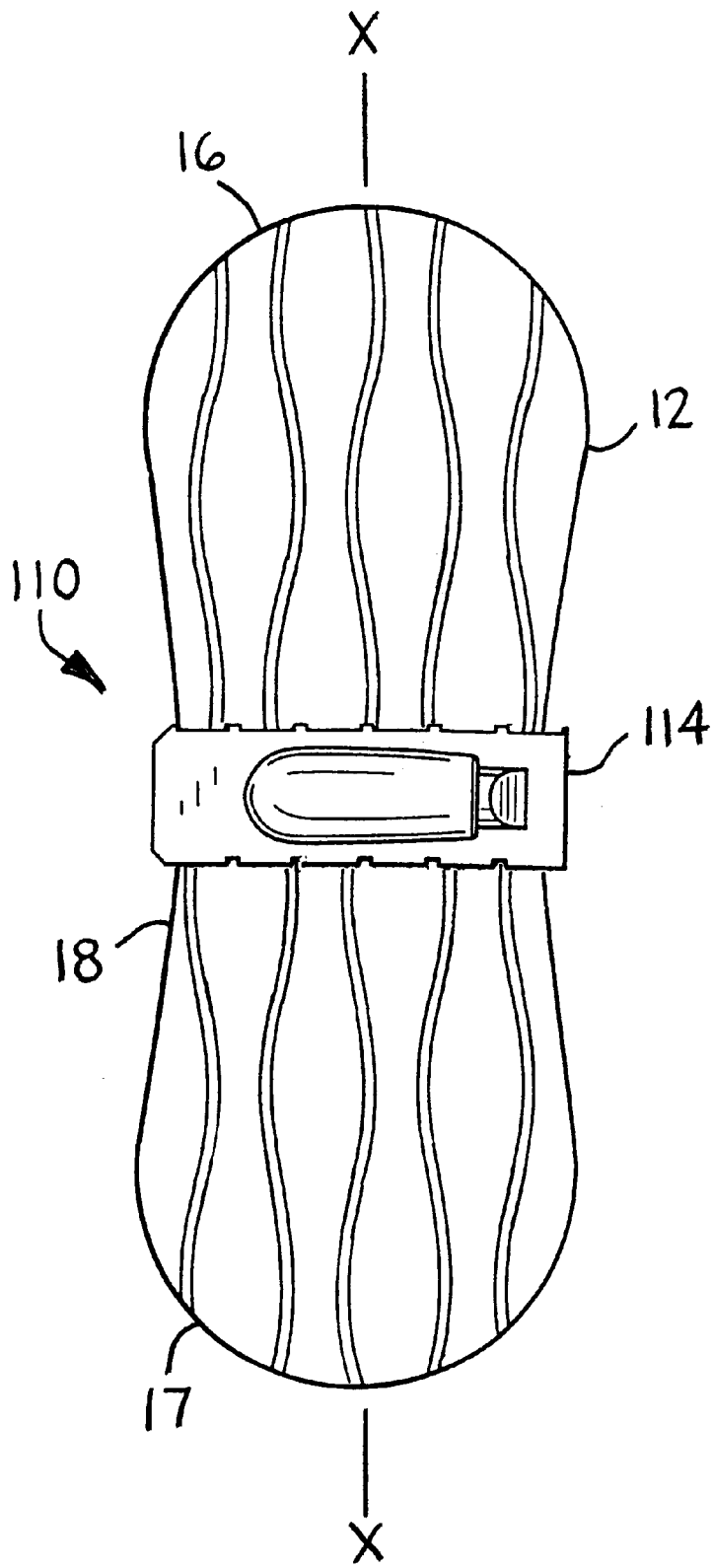
FIG. 5 illustrates an elevational view of a combination of a panty shield and a vaginal suppository.

Referring now to FIG. 5, there is illustrated a vaginal suppository 114 that can be similarly used with panty shield 12 by substituting suppository 114 for, by way of example, tampon 14 in FIG. 1 or tampon applicator 33 in FIG. 4. Vaginal suppository 114 is then folded over by the panty shield 12 in a similar manner, and can be packaged in a pouch 23, similar to that illustrated in FIG. 3.

Figure 6:
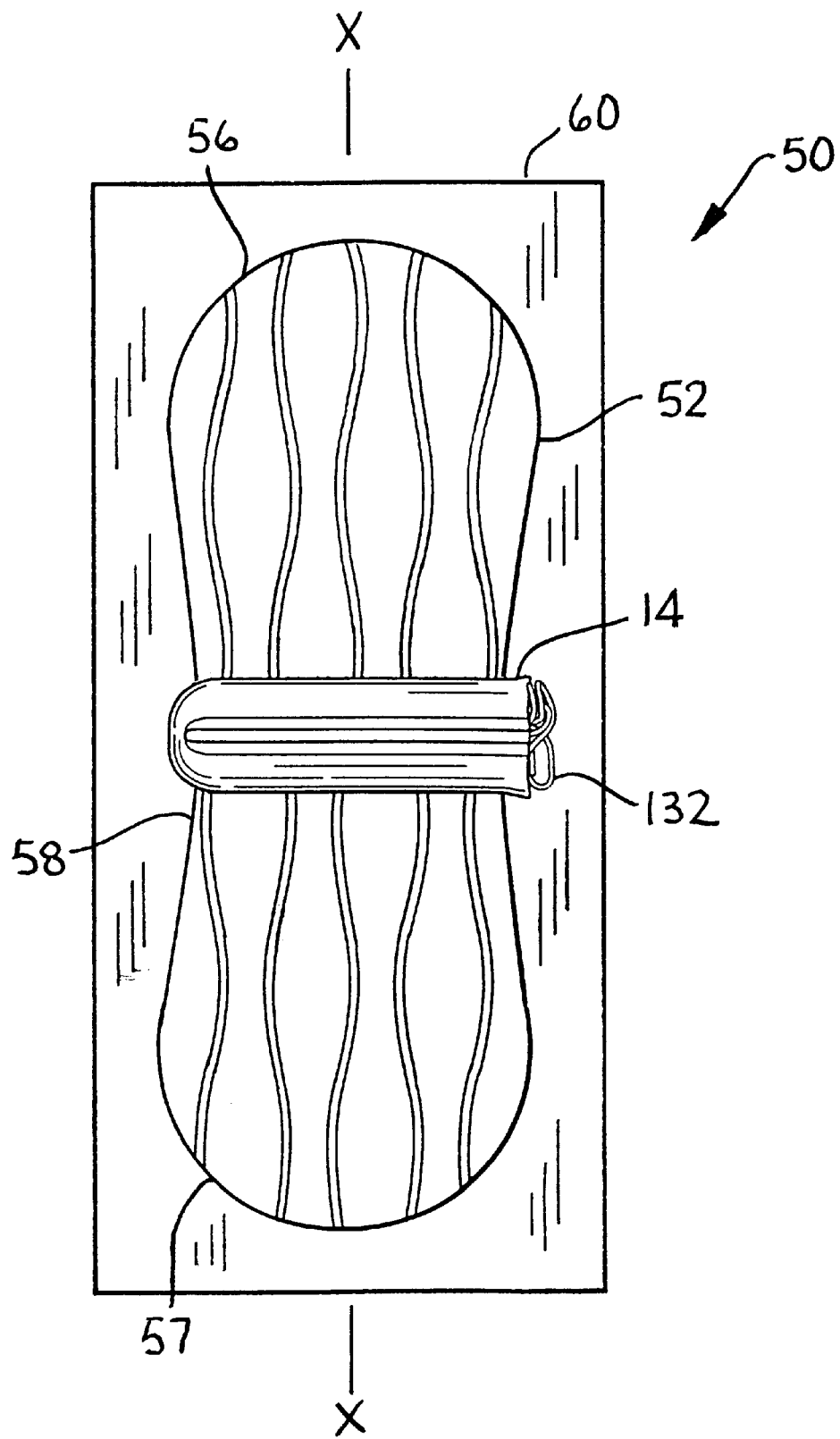
FIG. 6 illustrates an elevational view of a combination of another panty shield and a tampon.
Figure 7:
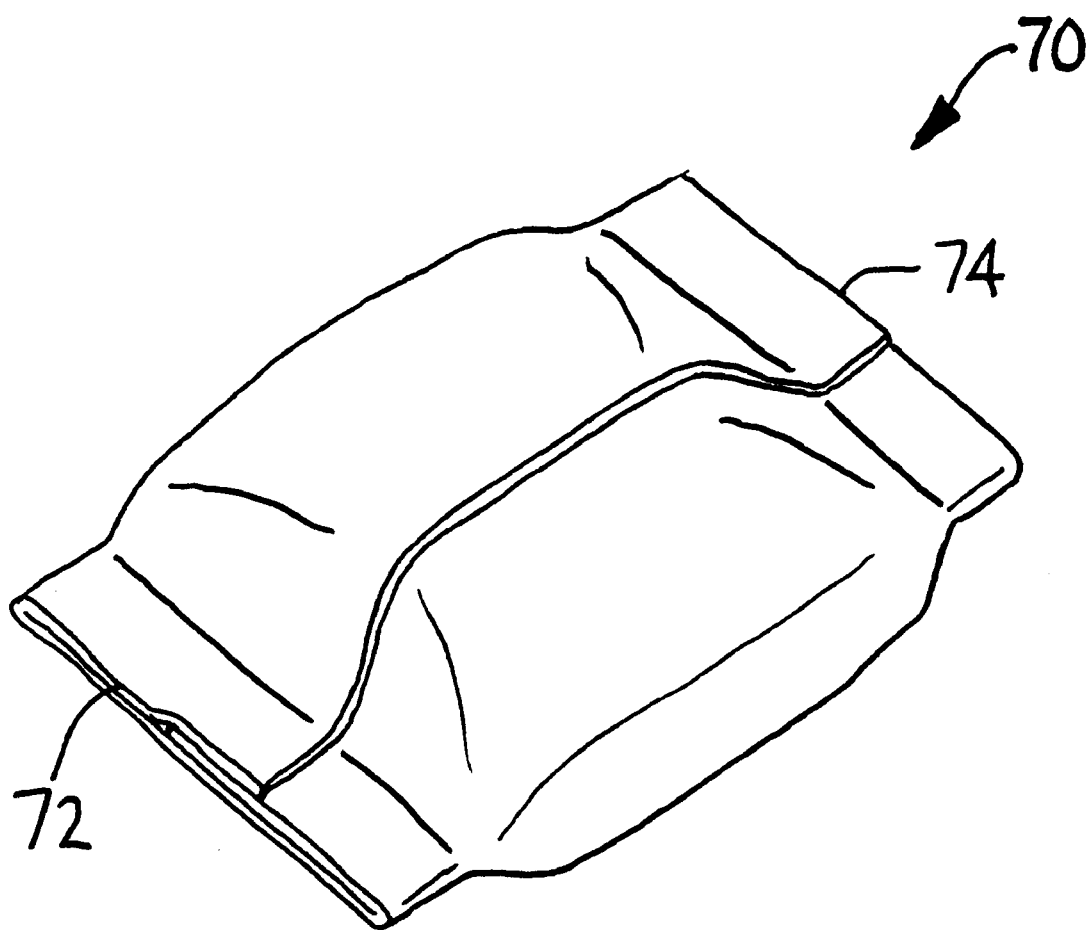
FIG. 7 illustrates the combination of FIG. 6 formed into a pouch.

Referring now to FIGS. 6 and 7, a sanitary protection device 50 includes a panty shield 52 and a vaginal insertion device, such as a tampon 14. The panty shield 52 can have an oval, straight, racetrack, hourglass, or other shape with a first end 56, a second end 57, and a middle section 58. The panty shield 52 has a central longitudinal axis X—X. The panty shield 52 has a backing 60 made of a material preferably composed of a plastic material such as polyethylene or polypropylene, but may be composed of other materials, e.g., such as polyethylene oxide (PEO), polyvinyl alcohol (PVOH), polycaporolactone (PCL), paper, or a nonwoven material, e.g., such as spunbond/meltblown.

The backing 60 protects the adhesive side of the panty shield 52 so that the adhesive remains clean and uncontaminated prior to attachment of the panty shield 52 to the crotch of a wearer's panty. The backing 60 is oversize in the sense that it is larger in dimension than the panty shield 52. The backing 60 can be rectangular in shape having dimensions in the range of about 17–21 centimeters (cm) in length and about 6.5 to 10.5 cm in width, as compared to a panty shield 52 having dimensions of about 16 cm in length and about 5.5 cm in width. Since the dimensions of the panty shield 52 can vary, the backing 60 can have dimensions in the range of about 1–5 cm more in length and about 1 to 5 cm more in width than the panty shield 52. By oversize dimension, it is meant larger than the panty shield 52. The purpose of the oversize dimension of backing 60 is to provide for the packaging pouch of the present invention.

The tampon 14 is shown placed in a position near the middle section 58 and is positioned generally transverse to the length of the device 50 and to the central longitudinal axis X—X. The panty shield 52 is tri-folded over the tampon 14 in a manner similar to that of panty shield 12 and tampon 14 in FIG. 1. The backing 60 is then suitable bonded in order to form a pouch 70 as illustrated in FIG. 7. Thus, the folded pouch 70 is formed of backing 60. The folded pouch 70 can be closed and suitable sealed at both ends 72 and 74 after the panty shield 52 is folded over tampon 14. The folded pouch 70 can be closed and sealed at both ends 72 and 74 by ultrasonic sealing, heat sealing, adhesive, embossing, or any other means well known in the art.

The backing 60 protects the adhesive side of the panty shield 52 and eliminates the need for a release strip on the adhesive backed panty shield. The pouch 70 serves as a transporting and disposing medium, which is sealed to protect the cleanliness of the panty shield 52 and tampon 14.

The backing 60 is designed to serve as a releasable peel strip to be removed by the user prior to attachment of the shield 52 to the inner crotch portion of her undergarment. The backing 60 can be a white Kraft paper which is coated on one side so that it can be released readily from the adhesive side of the panty shield 52. The coating can be a silicone coating, such as a silicone polymer commercially available from Akrosil having an office located at 206 Garfield Avenue, Menasha, Wis. 54952.

In a manner similar to that described in FIGS. 6 and 7 with reference to tampon 14, a tampon applicator 33 comprising an outer tube 34 and an inner tube 35 (FIG. 4) can be substituted for tampon 14 in FIGS. 6 and 7. Thus, the folded pouch 70 would then comprise the panty shield 52 and the tampon applicator 33.

Again, in a similar manner, a vaginal suppository, similar to suppository 114 in FIG. 5, can be substituted for the tampon in FIG. 6. Thus, the folded pouch 70 then comprises the panty shield 52 and the vaginal suppository 114.

If desired, the vaginal suppository 114 can also include an outer tube and a plunger, similar to that of tube 34 and plunger 35 in FIG. 4, and then tri-folded with the panty shield 12 of FIG. 1 or FIG. 6.

One construction and material composition of a panty shield 12 is the absorbent pad described in U.S. Pat. No. 4,372,312, which issued Feb. 8, 1983; the contents of which are incorporated by reference herein. Another example of a panty shield is the absorbent pad described in U.S. Pat. No. 3,881,490, which issued on May 6, 1975; the contents of which are incorporated by reference herein. One example of the construction and material composition of a tampon is the tampon described in U.S. Pat. No. 5,807,372, which issued Sep. 15, 1998; the contents of which are incorporated by reference herein.

While this invention has been described as having a preferred embodiment, it will be understood that it is capable of further modifications. It is therefore intended to cover any variations, equivalents, uses, or adaptations of the invention following the general principles thereof, and including such departures from the present disclosure as come or may come within known or customary practice in the art to which this invention pertains and falls within the limits of the appended claims.

What is claimed is:

1. A feminine sanitary protection package, comprising:
   a vaginal insertion device;
   a panty shield being tri-folded over said vaginal insertion device to form a combination including said panty shield and said vaginal insertion device; and
   a pouch containing said combination, said pouch providing for transporting and disposing of said combination.

2. The package of claim 1 wherein said vaginal insertion device comprises a tampon.

3. The package of claim 1 wherein said vaginal insertion device comprises a vaginal suppository.

4. The package of claim 2 wherein said vaginal insertion device further comprises a tampon applicator.

5. The package of claim 3 wherein said vaginal insertion device further comprises a vaginal suppository applicator.

6. The package of claim 1 wherein said pouch provides a release strip for said panty shield.

7. A method for providing a feminine care sanitary protection package comprising the steps of:
   providing a vaginal insertion device;
   providing a panty shield;
   tri-folding the panty shield over the vaginal insertion device to form a combination including the panty shield and the vaginal insertion device; and
   providing a pouch for the combination for transporting and disposing of the combination.

8. The method of claim 7 wherein the vaginal insertion device comprises a tampon.

9. The method of claim 7 wherein the vaginal insertion device comprises a vaginal suppository.

10. The method of claim 8 wherein the vaginal insertion device further comprises a tampon applicator.

11. The method of claim 9 wherein the vaginal insertion device further comprises a vaginal suppository applicator.

12. A method for providing a feminine care sanitary protection package comprising the steps of:
   providing a vaginal insertion device;
   providing a panty shield having an attachment adhesive;
   tri-folding the panty shield over the vaginal insertion device to form a combination including the panty shield and the vaginal insertion device; and
   providing a pouch for the combination for transporting and disposing of the combination, the pouch being provided to contain the combination such that the pouch is adapted to serve as a release strip for the attachment adhesive on the panty shield.

13. A feminine sanitary protection package, comprising;
   a vaginal insertion device,
   a panty shield being folded over said vaginal insertion device to form a combination including said panty shield and said vaginal insertion device;
   a release strip on said panty shield; and
   a pouch providing for transporting and disposing of said combination.

14. The package of claim 13 wherein said vaginal insertion device comprises a tampon.

15. The package of claim 13 wherein said vaginal insertion device comprises a vaginal suppository.

16. The package of claim 14 wherein said vaginal insertion device further comprises a tampon applicator.

17. The package of claim 15 wherein said vaginal insertion device further comprises a vaginal suppository applicator.

18. A feminine sanitary protection package, comprising:

a vaginal insertion device;

a panty shield being folded over said vaginal insertion device to form a combination including the panty shield and the vaginal insertion device;

an attachment adhesive on the panty shield; and a pouch providing for transporting and disposing of the combination, wherein the pouch contains the combination of panty shield and vaginal insertion device such that the pouch is adapted to serve as a release strip for the attachment adhesive on the panty shield.

\* \* \* \* \*